United States Patent [19]

Lee

[11] Patent Number: 4,509,856
[45] Date of Patent: Apr. 9, 1985

[54] ROTOR FOR CENTRIFUGAL FAST ANALYZERS

[75] Inventor: Norman E. Lee, Knoxville, Tenn.

[73] Assignee: The United States of America as represented by the United States Department of Energy, Washington, D.C.

[21] Appl. No.: 442,065

[22] Filed: Nov. 16, 1982

[51] Int. Cl.³ .............................................. G01N 1/10
[52] U.S. Cl. .................................. 356/246; 250/461.1; 422/72
[58] Field of Search .................... 356/246, 426, 427; 250/461.1, 461.2, 576; 422/64, 72, 102; 436/45

[56] References Cited

U.S. PATENT DOCUMENTS

| | | | |
|---|---|---|---|
| 3,555,284 | 1/1971 | Anderson | 356/246 X |
| 3,798,459 | 3/1974 | Anderson et al. | 250/576 |
| 3,804,533 | 4/1974 | Scott | 356/246 X |
| 4,431,606 | 2/1984 | Revillet et al. | 356/246 X |

OTHER PUBLICATIONS

Burtis et al., "Development of a Multipurpose Optical System for Use with a Centrifugal Fast Analyzer", *Clin. Chem.*, vol. 21, No. 9, pp. 1225–1233, 1975.

Hills et al., "Comparison of Turbidimetric and Light-Scattering Measurements . . . ", *Clin. Chem.*, vol. 26, No. 10, pp. 1459–1466, 1980.

*Primary Examiner*—Vincent P. McGraw
*Assistant Examiner*—Matthew W. Koren
*Attorney, Agent, or Firm*—Fred O. Lewis; Stephen D. Hamel

[57] ABSTRACT

The invention is an improved photometric analyzer of the rotary cuvette type, the analyzer incorporating a multicuvette rotor of novel design. The rotor (a) is leaktight, (b) permits operation in the 90° and 180° excitation modes, (c) is compatible with extensively used Centrifugal Fast Analyzers, and (d) can be used thousands of times. The rotor includes an assembly comprising a top plate, a bottom plate, and a central plate, the rim of the central plate being formed with circumferentially spaced indentations. A UV-transmitting ring is sealably affixed to the indented rim to define with the indentations an array of cuvettes. The ring serves both as a sealing means and an end window for the cuvettes.

9 Claims, 3 Drawing Figures

ROTOR FOR CENTRIFUGAL FAST ANALYZERS

BACKGROUND OF THE INVENTION

This invention relates generally to centrifugal fast analyzers of the rotary cuvette type and more particularly to improved rotors for the same. The invention is a result of a contract with the United States Department of Energy.

The Centrifugal Fast Analyzer (CFA) is a photometric instrument which typically includes a rotatable multicuvette assembly (rotor), a source for directing an optical beam into the cuvettes of the spinning rotor, a stationary optical detector for receiving light signals from the spinning cuvettes, and on-line data processing equipment for processing the signals.

Some 40,000 "standard" CFA's are presently in use. Briefly, the typical standard CFA employs a disk-shaped plastic rotor consisting of a central body sandwiched between two transparent covers. The central body is designed with three sets of chambers disposed in respective circular arrays: an inner array, an intermediate array, and an outer array (which consists of sample-analysis chambers, or cuvettes). The chambers in the three arrays are disposed in radial rows. Elevated passages in the central body connect the inner chambers to the intermediate chambers, and the latter to the cuvettes. With the rotor stationary, liquid reagents are introduced to the inner chambers, and other liquid reagents are introduced to the intermediate chambers. The rotor then is spun to generate sufficient centrifugal force to (a) transfer liquid from the inner chambers to the intermediate chambers, initiating reaction of the reagents, and (b) transfer the resulting solutions into the cuvettes for analysis by photometric techniques.

The following article, which is incorporated herein by reference, describes a "standard" CFA and various interchangeable rotors for use therein: "Development of a Multipurpose Optical System for Use with a Centrifugal Fast Analyzer", *Clinical Chemistry*, Vol. 2, No. 9, 1975. That CFA utilizes a photodetector which is positioned below the rotor to receive light signals from the cuvettes. The light source is designed so that the incident optical beam may be directed into the cuvettes of the spinning rotor in either a 180° or a 90° orientation, relative to the photodetector. Excitation in the 180° mode (light directed downwardly through the cuvettes) is provided for absorbance measurements, in which case the rotor consists throughout of clear acrylic plastic, which transmits ultraviolet light (UV). Excitation in the 90° mode (light introduced transversely) is provided for fluorescence measurements, in which case the covers of the rotor may consist of clear acrylic plastic and the central body may consist of opaque acrylic plastic (to eliminate light transfer, or "crosstalk", between adjacent cuvettes).

The above-mentioned article points out that 90° excitation should provide high sensitivity for fluorescence measurements because of decreased interference from reflected incident radiation. It describes an "insert" rotor designed especially for such use. This rotor included clear, UV-transmitting plastic covers and a central body composed of black plastic. The outer wall portion of each cuvette was drilled through to provide a radially extending opening, and a quartz cylinder (end window) was fitted in each such opening and sealed in place. Unfortunately, this rotor developed leaks when spun; some of the quartz cylinders loosened to the extend that they were flung out of the rotor wall. Consequently, the insert rotor was abandoned.

Another centrifugal analyzer utilizing a multicuvette rotor is described briefly in the following publication: "Comparison of Turbidimetric and Light-Scattering Measurements of Immunoglobulins by Use of a Centrifugal Analyzer with Absorbance and Fluorescence/Light-Scattering Optics", *Clinical Chemistry*, Vol. 26, No. 10 (1980). That analyzer is designed to operate with either 180° excitation or 90° excitation. The disk-shaped rotor assembly includes a cast, disposable central body composed of clear plastic and carrying a circular array of spaced cuvettes which extend downwardly from the underside of the body. Each cuvette is formed with top, bottom, and end windows of polished acrylic. Such rotors are subject to some limitations: they are not designed for long-term use; they are not compatible with the standard CFA's referred to above; and they do not achieve maximum sensitivity for fluorescence measurements because some crosstalk occurs between adjacent cuvettes.

SUMMARY OF THE INVENTION

Accordingly, it is an object of this invention to provide a novel rotor for use in standard Centrifugal Fast Analyzers.

It is another object to provide a rotor which (a) is compatible with standard CFA's; (b) permits either 90° excitation or 180° excitation; (c) is leaktight; and (d) can be used thousands of times.

Other objects and advantages will be made evident hereinafter.

The invention is a photometric analyzer of the rotary cuvette type, the analyzer including a rotor which comprises an assembly including a top plate, a bottom plate, and a central plate. The rim of the central plate is formed with circumferentially spaced indentations. A ring composed of UV-transmitting material is sealably affixed to the rim of the central plate to define therewith a circular array of cuvettes. In another aspect, the central plate is composed of a non-UV transmitting material.

DETAILED DESCRIPTION OF THE INVENTION

Figure 1:
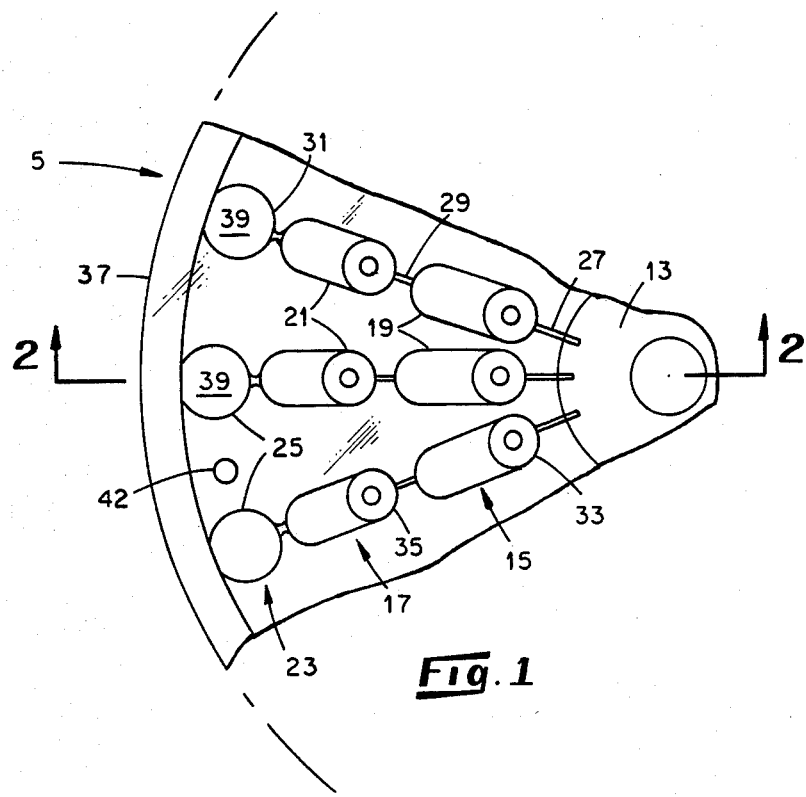
FIG. 1 is a plan view of a typical segment of a leaktight rotor designed in accordance with the invention, the rotor being compatible with the above-mentioned standard Centrifugal Fast Analyzers and being usable in either the 90° excitation mode or the 180° excitation mode.
Figure 2:
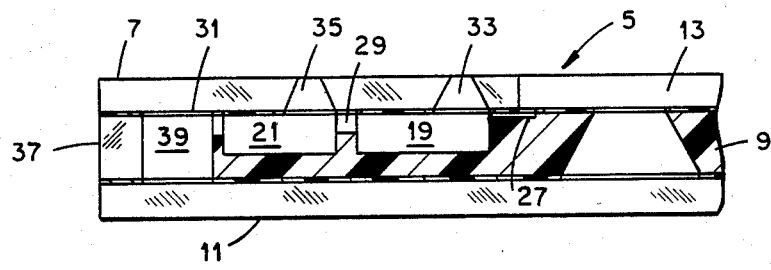
FIG. 2 is a section view taken along line 2—2 of FIG. 1.

Referring to the drawings, a preferred embodiment of the photometric analyzer (4, FIG. 3) includes a rotor which comprises a circular-plate assembly 5. The assembly includes a transparent top plate 7, an opaque central plate 9, and a transparent bottom plate 11. The three plates are composed of a rigid and optically suitable material, such as acrylic plastic. As shown in FIG. 2, the central plate 9 has a smaller diameter than the other plates. The upper surface of the central plate is formed with two circular arrays 15 and 17 of radially extending chambers, 19 and 21, respectively. In accordance with the invention, the rim of plate 9 is formed with a circular array 23 of indentations 25; in the embodiment shown, each indentation extends transversely and defines an arc of about 80°. The chambers and indentations of the three circular arrays are disposed in radial rows. Each row includes three radially extending surface grooves: a groove 27 connecting the inner end of chamber 19 to the central region of plate 7; a groove 29 interconnecting the chambers 19 and 21; and a groove 31 connecting chamber 21 to the indentation 25.

The top and bottom plates 7 and 11 may be of standard design. As shown, the top plate is provided with two circular arrays of tapered bores 33 and 35 for introducing liquids to the chambers 19 and 21, respectively, when the assembly is at rest. The top plate 7 is formed with a central aperture which, together with the plate 9, defines a central recess 13 communicating with the grooves 27. In the embodiment shown, the bottom plate has no chambers or grooves. The plate assembly 5 is formed with two diametrically opposed throughgoing bores 42 (only one of which is in view). These are sized to receive mounting pins provided on any suitable rotor drive means (41, FIG. 3), such as the drive used with the standard CFA's referred to above.

In accordance with the invention, a ring 37, composed of acrylic plastic or some other suitable UV-transmitting material is fitted between the projecting edges of the top and bottom plates 7 and 11 and is sealed to the indented rim of the central plate 9. The ring serves as a leaktight, UV-transmitting end window for each of the cuvettes, permitting the rotor assembly to be used for 90° excitation fluorescence measurements, as well as the usual 180° excitation measurements. When used with a laser for 90° excitation, a rotor of the kind described (opaque central body 9, UV-transmitting ring 37, etc.) provides an improvement in fluorescence detection of from 50–100 times, as compared with a standard rotor having a clear central body and using a non-laser light source. The new rotor can be used thousands of times at speeds of rotation typical for CFA's.

The entire assembly 5 may be fabricated by conventional machining operations or by any other suitable technique. For instance, the central plate with its indentations 25 may be formed by machining or casting. Alternatively, the indented plate may be formed by machining away the rim of a conventional one-piece, opaque central body designed for use in standard CFA's. The ring 37 may be sealably joined to the indented rim of the plate in any suitable manner; preferably, this is accomplished by solvent-bonding with ethylene dichloride. The ring may be composed of any suitable UV-transmitting material and conceivably could be fabricated from quartz. Preferably, the ring is not solvent-bonded to the top and bottom plates 7 and 11, so that the same central body-and-ring assembly may be used with interchangeable top and bottom plates. The top and bottom plates may be sealed to the central body with Dow Corning 3145 RTV Adhesive/Sealant and subsequently may be removed by soaking the rotor assembly in methyl alcohol for about thirty minutes.

The new rotor described herein may be employed in the usual fashion. For example, before rotation the chambers 19 may be filled with liquid samples, and the chambers 21 with liquid agents for reacting therewith. When the loaded rotor is spun at suitable speed, centrifugal force causes the samples to flow into chambers 21 via the grooves 29 and causes the resulting mixture of sample and reaction agent to flow through the grooves 31 into the cuvettes 39, for photometric analysis.

Figure 3:
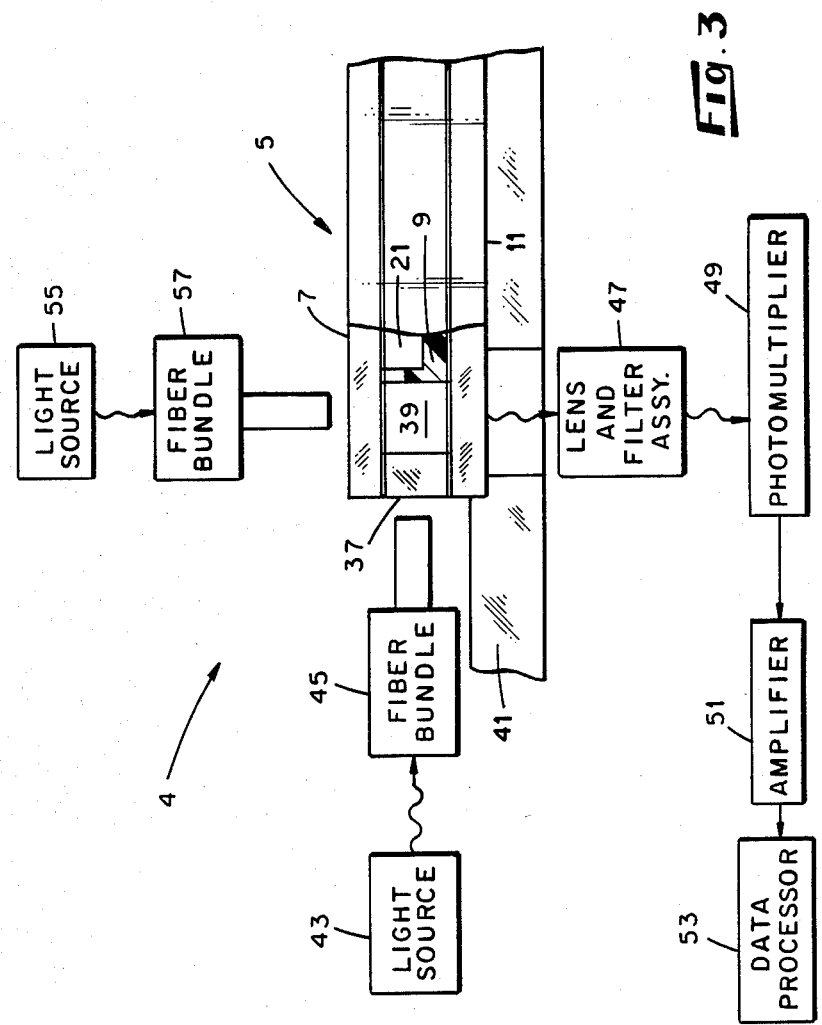
FIG. 3 is a schematic diagram illustrating how the invention may be utilized in standard CFA systems.

FIG. 3 illustrates the rotor 5 as utilized in an otherwise-conventional CFA including a light source 43 (preferably a laser) and an optical-fiber bundle 45 for 90° excitation of a sample in the cuvette 39. As shown, the incident laser beam emerges downwardly from the cuvette, passing through a lens and filter assembly 47 to a photomultiplier tube 49. The output from the photomultiplier is fed, via an amplifier 51, to a data-processing device 53, such as a computer. For 90° excitation analyses, the top plate 7 may be opaque or reflective. Also shown is an alternative arrangement provided for 180° excitation analyses. That arrangement includes a light source 55 and an optical-fiber bundle 57.

The foregoing description of the preferred embodiment of the invention is not intended to be exhaustive or to limit the invention to the precise form disclosed. Obviously, many modifications and variations are possible in light of the above teaching. It is intended that the scope of the invention be defined by the claims appended hereto.

What is claimed is:

1. In a photometric analyzer of the rotary cuvette type:
    a rotor comprising an assembly including a top plate, a bottom plate, and a central plate, the rim of said central plate being formed with circumferentially spaced indentations, and
    a ring composed of UV-transmitting material sealably affixed to said rim and defining therewith a circular array of cuvettes.

2. The analyzer of claim 1 wherein said indentations define an arc.

3. The analyzer of claim 1 wherein said central plate is composed of opaque material.

4. In a photometric analyzer of the rotary cuvette type:
    a rotor comprising a circular-plate assembly including top and bottom cover plates and also including a central plate composed of non-UV-transmitting material mounted between said cover plates; the rim of said central plate being formed with circumferentially spaced arcuate indentations extending transversely thereof, and
    a UV-transmitting ring sealably engaging said rim and defining with said indentations a circular array of cuvettes.

5. The analyzer of claim 4 wherein said cuvettes have a generally circular side wall.

6. The analyzer of claim 4 wherein said ring is bonded to said rim.

7. In a photometric analyzer of the rotary cuvette type:
    a rotor comprising a plate assembly including a top plate, a UV-transmitting bottom plate, and an opaque central plate having a smaller diameter than said top plate and bottom plate and having a rim which is formed with circumferentially spaced, transversely extending indentations, said central plate also being formed with an array of chambers which communicate respectively with said indentations via channels formed in said central plate, and
    a UV-transmitting ring fitted between said top plate and bottom plate and sealably affixed to said rim, said ring and indentations cooperatively defining an array of cuvettes.

8. The analyzer of claim 7 wherein said chambers are recesses in the upper surface of said central plate.

9. The analyzer of claim 7 wherein said ring is bonded to said rim.

* * * * *